United States Patent [19]
Barsky et al.

[11] Patent Number: 5,758,096
[45] Date of Patent: May 26, 1998

[54] SYSTEM AND METHOD FOR PERSONALIZED MEDICATION TREATMENT MANAGEMENT

[76] Inventors: Howard Barsky; Nina E. Barsky; Daniel M. Barsky, all of 9258 Airdrome St., Los Angeles, Calif. 90035

[21] Appl. No.: 513,014

[22] Filed: Aug. 9, 1995

[51] Int. Cl.⁶ .................. G06F 3/14; G06F 17/00
[52] U.S. Cl. .................. 395/203; 283/115; 283/900
[58] Field of Search .................. 395/202, 203; 364/413.02; 283/115, 900

[56] References Cited

U.S. PATENT DOCUMENTS

| | | |
|---|---|---|
| 4,389,963 | 6/1983 | Pearson .................. 116/308 |
| 4,815,767 | 3/1989 | Lambert .................. 283/67 |
| 5,261,702 | 11/1993 | Mayfield .................. 283/115 |

OTHER PUBLICATIONS

Webster'II, New Riverside University Dictionary, 1994.

*Primary Examiner*—Gail O. Hayes
*Assistant Examiner*—Barton L. Bainbridge
*Attorney, Agent, or Firm*—John L. Rogitz

[57] ABSTRACT

A computer-based system and method for generating a medication management display comprises entering a plurality of medication names prescribed for one or more patients, with corresponding strength attributes, and alpha-numeric medication symbol attributes, into an electronic data base. An electronically stored correlation list is then accessed to associate the alpha-numeric symbol attributes to graphic symbols. This information is arranged to generate a patient medication chart displaying one or more medication names associated with its corresponding strength, directions, and graphic symbol. Adhesive graphic symbols are applied to the original medication containers that hold the medications to cross reference the actual medications with the chart. The patient medication data may also include administration comments with at least one medication which is visually displayed.

8 Claims, 6 Drawing Sheets

| Medication | Strength | Letter code | Directions | after Waking | Breakfast | bet b'fast & lunch | Lunch | bet lunch & dinner | Dinner | Bedtime | Comments |
|---|---|---|---|---|---|---|---|---|---|---|---|
| DIGOXIN | .125 MG | A | 2 PILLS EVERY MORNING | | (A)—74 | | | | | | |
| THEODUR | 300 MG | B | 1/2 PILL, 2 TIMES DAILY | | (B)—106 | | | | (B) | | 6/8 START 1/2 PILL 2XDAY |
| HYDRALAZINE | 25 MG | C | 1 PILL, 4 TIMES DAILY | | (C) | | (C) | | (C) | (C) | |
| LAMISIL CREAM | 1% | D | BETWEEN TOES IN AM | (D) | | | | | | | |
| GLY-OXIDE | Liquid Peroxi | E | 10 DROPS IN MOUTH EVERY MORNING AND EVENING | (E) | | | | | 100 | (E) | |
| STOOL SOFTENER | 100 MG | F | 1 PILL TWICE DAILY | | (F) | | | | (F) | | |
| VANCERIL INHALER | BROWN CONTAL | G | 4 PUFFS, 4 TIMES DAILY | | (G) | (G) | (G) | | (G) | | RE-START 7/8 |
| VERAPAMIL (CALAN) | 80 MG | H | 1, 2 TIMES DAILY | | (H) | | | | (H) | | TOTAL 150 MG A DAY |
| LEVOTHROID | .025 MG | J | ALTERNATE 2 PILLS, 3 PILLS DAILY WITH BREAKFAST | | (J)→ SEECOMMENT | | | | | | 2 PILLS EVEN DATES, 3 PILLS ODD DATES |
| AMIODARONE (CORDARONE) | 200 MG | K | 1, EVERY MORNING | | (K) | | | | | | |
| PROVENTIL INHALER | PULM O-AID | L | 1 CONTAINER, 4 TIMES A DAY | | (L) | (L) | (L) | | (L) | | |
| POTASSIUM CHLORIDE | 10% SOLUTI | M | 1 TBLSP, TWICE DAILY IN GLASS OF JUICE PROV | | (M) | | | | (M) | | |

PATIENT NAME: JANE DOE
REQUESTED BY:
DATE REQUESTED: JUL 28, 1995
CHART PRINT DATE: 7/28/95
CHART I.D. # DOE A

NOTES

Fig. 2

ENTRY OPR Example
REQUESTED BY
PATIENT FIRST NAME Jane   28  Doe
DATE REQUESTED 07/28/95

I.D. = LLLLFddmmyy
4 LETTERS LAST NAME, ONE LETTER FIRST NAME, DAY MONTH YEAR
CHART I.D. # DOE J072895

| | Medication | Strength | Directions | Time of Day → | after Waking | Breakfast | bet b'fast & lunch | Lunch | bet lunch & dinner | Dinner | Bedtime | Comm. |
|---|---|---|---|---|---|---|---|---|---|---|---|---|
| A | DIGOXIN | .125 MG | 2 PILLS EVERY MORNING | | | b = c1 | | | | | | |
| B | THEODUR | 300MG | 1/2 PILL, 2 TIMES DAILY | | | c1 | | c1 | | b = c1 | | 6/8 START 1/2 |
| C | HYDRALAZINE | 25MG | 1 PILL, 4 TIMES DAILY | | | c1 | | c1 | | c1 | c1 | |
| D | LAMISIL | 1% | BETWEEN TOES IN AM | | D crm | | | | | | | |
| E | GLY-OXIDE | LIQUID PERO | 10 DROPS IN MOUTH | | e drp | | | | | | e drp | |
| F | STOOL | 100 MG | 1 PILL TWICE DAILY | | | f1 | | | | f1 | | |
| G | VANCERIL | BROWN | 4 PUFFS, 4 TIMES DAILY | | g inh | | g inh | | g inh | | g inh | |
| H | VERAPAMIL | 80 MG | 1, 2 TIMES DAILY | | | h1 | | | | h1 | | RE-START 7/8 TOTAL 160 MG 2 PILLS EV. |
| J | LEVOTHROID | .025 MG | ALTERNATE 2 PILLS, 3 PILLS | | | j see | | | | | | |
| K | AMIODARONE | 200 MG | 1, EVERY MORNING | | | k1 | | | | | | |
| L | PROVENTIL | PULMO- | 1 CONTAINER, 4 TIMES A | | l pul | | l pul | | l pul | | l pul | |
| M | POTASSIUM | 10% | 1 TBLSP, TWICE DAILY IN | | | m mix | | | | m mix | | |

NOTES

PATIENT NAME: JANE DOE
REQUESTED BY:
DATE REQUESTED: JUL 28, 1995
CHART PRINT DATE: 7/28/95    DOE A
CHART I.D. #   108

| Medication | Strength | Letter code | Directions | after Waking | Breakfast | bet b'fast & lunch | Lunch | bet lunch & dinner | Dinner | Bedtime | Comments |
|---|---|---|---|---|---|---|---|---|---|---|---|
| DIGOXIN | .125 MG | A | 2 PILLS EVERY MORNING | | Ⓐ | 74 | | | | | |
| THEODUR | 300 MG | B | 1/2 PILL, 2 TIMES DAILY | | Ⓑ | 106 | | | Ⓑ | | 6/8 START 1/2 PILL 2×DAY |
| HYDRALAZINE | 25 MG | C | 1 PILL, 4 TIMES DAILY | Ⓓ | Ⓒ | | Ⓒ | | Ⓒ | Ⓒ | |
| LAMISIL CREAM | 1% | D | BETWEEN TOES IN AM | Ⓔ | | | | | | | |
| GLY-OXIDE | Liquid Peroxi | E | 10 DROPS IN MOUTH EVERY MORNING AND EVENING | Ⓖ | | Ⓖ | | | | Ⓔ | |
| STOOL SOFTENER | 100 MG | F | 1 PILL TWICE DAILY | | Ⓕ | | | | Ⓕ | | |
| VANCERIL INHALER | BROWN CONTAL | G | 4 PUFFS, 4 TIMES DAILY | | | | | Ⓖ | | Ⓖ | RE-START 7/8 |
| VERAPAMIL (CALAN) | 80 MG | H | 1, 2 TIMES DAILY | | Ⓗ | | | | Ⓗ | | TOTAL 150 MG A DAY |

| | | | | | | | | | 2 PILLS EVEN DATES, 3 PILLS ODD DATES |
|---|---|---|---|---|---|---|---|---|---|
| LEVOTHROID | .025 MG | | ALTERNATE 2 PILLS, 3 PILLS DAILY WITH BREAKFAST | (J) ↑ SEE COMMENT | | | | | |
| AMIODARONE (CORDARONE) | 200 MG | (K) | 1, EVERY MORNING | (K) | | | | | |
| PROVENTIL INHALER | PULM O-AID | (L) | 1 CONTAINER, 4 TIMES A DAY | | | | | | |
| POTASSIUM CHLORIDE | 10% SOLUTI | (M) | 1 TBLSP, TWICE DAILY IN GLASS OF JUICE PROV | | | | | | |

NOTES

Fig. 5B

Medication List

Fig. 6

PATIENT NAME: _______________ FIRST _______________ MIDDLE INITIAL _______________ LAST

DATE: _______________
EVENING PHONE: ( ) _______________
DAYTIME PHONE: ( ) _______________

MAILING ADDRESS: STREET ADDRESS OR P.O. NUMBER _______________ CITY _______________ STATE _______________ ZIP _______________

PERSON MAKING THIS REQUEST: PRINT NAME PLEASE _______________ SIGNATURE (REQUIRED) _______________ DATE _______________

| MEDICATION | STRENGTH | IN WHAT FORM IS MEDICATION | DIRECTIONS (AS IS TYPED ON MEDICATION) | OTHER INSTRUCTIONS ON MEDICATION | WHEN DO YOU ACTUALLY TAKE MEDICATION |
|---|---|---|---|---|---|
| *EXAMPLES* | | | | | *EXAMPLES* |
| ISORDIL | 20MG | TABLET | 1 TABLET, THREE TIMES DAILY | TAKE WITH FOOD | I TAKE THEM WITH MEALS |
| POTASSIUM CHLORIDE | 10% | LIQUID | 1 TBLSP TWICE DAILY IN LIQUID | STOP 12/31/94 | 1 W/ BKFST, 1 AT BEDTIME |
| ATROVENT | | INHALER | 2 PUFFS, 4 TIMES A DAY | FOLLOW DIRECTIONS CAREFULLY | AFTER MEALS AND AT BEDTIME |
| LAMISIL | 1% | CREAM | APPLY BETWEEN TOES TWICE A DAY | FOR TOPICAL USE ONLY | IN MORNING AND BEDTIME |
| 1 | | | | | |
| 2 | | | | | |
| 3 | | | | | |
| 4 | | | | | |
| 5 | | | | | |
| 6 | | | | | |
| 7 | | | | | |
| 8 | | | | | |
| 9 | | | | | |
| 10 | | | | | |
| 11 | | | | | |
| 12 | | | | | |

FOR MORE THAN 12 MEDICATIONS MAKE A COPY OF THIS SHEET BEFORE STARTING.

NOTES:

5,758,096

SYSTEM AND METHOD FOR PERSONALIZED MEDICATION TREATMENT MANAGEMENT

FIELD OF THE INVENTION

The present invention relates generally to medication treatment, and more particularly to systems and methods for managing a person's medication treatment.

BACKGROUND

Advances in biotechnology have made possible the development of many new and useful medications for treating a variety of maladies. One consequence of the growing number of useful medications is that a patient may be treated for one or more maladies with more than one medication.

Typically, medication treatment requires administering to a patient a specified dose of the medication at a specified periodicity. When the patient is being treated with more than a single medication, treatment might require that a first medication be administered in a first dosage at a first periodicity, and a second medication be administered in a second dosage at a second periodicity. It will readily be appreciated that when more than two medications are used to treat a patient, the task of properly managing the administration of the treatment is compounded. The fact that specified dosages and ingestion periodicities can frequently change increases the risk of treatment mismanagement. It is nevertheless crucial, however, to properly manage the treatment, because misadministration of medications can be harmful to the patient.

When the patient is an elderly outpatient who must administer many medications to himself or herself, the management problem is often compounded. Further, a caregiver in an inpatient facility who must administer many medications to many patients throughout the day faces a daunting treatment management task.

Accordingly, systems have been devised for supporting proper medication treatment management. For example, U.S. Pat. No. 5,621,702 discloses a medication management kit that includes an erasable plastic chart and a marking pen, and a list of medications with administration periodicities can be written by hand on the chart. The chart is intended to be mounted on a ferromagnetic surface, so that color-coded magnetized symbols can be positioned next to medication names to associate the symbols with respective medications. Corresponding color-coded tabs are adhesively applied to containers that hold the medications listed on the chart, so that a patient can associate the contents of a medication bottle with a treatment regime as specified on the chart.

Unfortunately, the kit disclosed in the '702 patent can become messy, and the symbols can be unintentionally separated from the chart. Further, no provision is made to customize the chart for a particular patient, other than by writing over inapplicable portions of the chart by hand. Moreover, the '702 invention does not consider dedicating a portion of the chart, other than a general "notes" section, to uniquely (and, thus, clearly and plainly) set forth specified medication strengths.

As recognized by the present invention but not by the '702 patent, these and other disadvantages can be overcome using computer technology to render a more effective, easily personalized and easily modified medication management system. Accordingly, it is an object of the present invention to provide a system for managing medication treatment which is easy to personalize. Another object of the present invention is to provide a system for managing medical treatment which clearly sets forth medication strengths and periodicities, and associates the strengths with the original containers that hold the medications. Yet another object of the present invention is to provide a system for managing medical treatment which is easy to use and cost effective.

SUMMARY OF THE INVENTION

A preferred embodiment of the method for generating a medication management display comprises the steps of entering a plurality of medication names prescribed for one or more patients, corresponding strength attributes, caregiver directions, and alpha-numeric medication symbol attributes, into an electronic data base. An electronically stored correlation list is then accessed to associate the alpha-numeric symbol attributes to graphic symbols. This information is arranged to generate a patient medication chart. The patient medication chart is a visual display which includes one or more medication names, with each name being visually associated with its corresponding strength and graphic symbol and caregiver directions. Adhesive graphic symbols are applied to appropriate containers containing the medication to cross reference the actual medications with the chart.

A preferred embodiment of the system for generating a medication management display comprises means for entering and storing patient medication data into an electronic data base. The patient medication data includes medication name attributes each representing a respective medication, a strength attribute corresponding to each name attribute, directions from a caregiver, and an alpha-numeric symbol attribute corresponding to each name attribute. Correlation means for accessing an electronically stored correlation list is associated with the patient medication data to associate the alpha-numeric symbol attribute to a graphic symbol. Display means is associated with the correlation means and stored patient data for generating a visual display. The visual display is in the form of a patient medication chart and includes one or more of the name attributes, in which each displayed name attribute is visually associated with its corresponding strength attributes, caregiver directions, and symbol. The system further comprises means for entering each symbol attribute in one or more columns of a spreadsheet having corresponding displayed time columns, so that the symbol is visually displayed in one or more displayed time columns. The system also includes labels having the various symbols displayed thereon, and the labels are placed on the appropriate medication container for visually associating the symbol with the medication having the same symbol displayed on the patient medication chart. The patient medication data may also include administration comments with at least one medication which is visually displayed.

In another aspect of the present invention, a computer-generated patient medication chart includes a substrate, and a columnar list of medications is superimposed on the substrate. A columnar list of strengths is visually associated with each medication. Also, a columnar list of direction entries is likewise superimposed on the substrate, with each entry in the list being visually associated with a respective medication. Further, a tabular time table is superimposed on the substrate, and the time table contains symbols, each of which indicates, by its position in the time table and by its configuration and color, a respective medication and time of ingestion for the medication. Preferably, a columnar comments list of comments can be selectively generated and visually associated with one or more of the medications in the list of medications.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
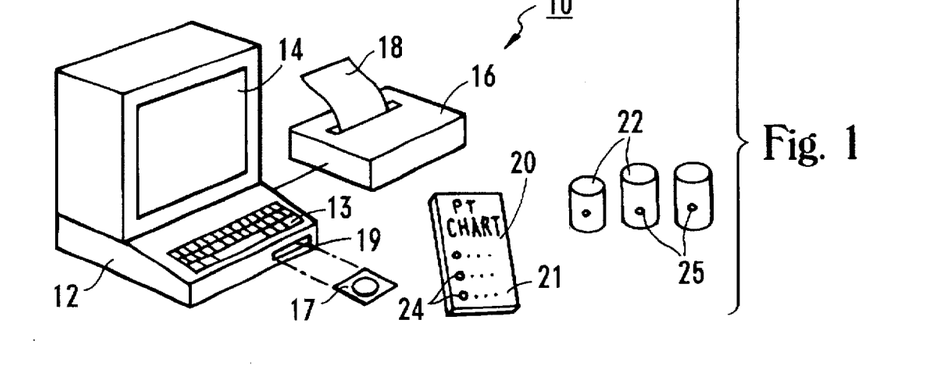
FIG. 1 is a perspective view of a patient medication treatment management system as used in its intended environment in accordance with the present invention.

Referring initially to FIG. 1, a personalized patient medication treatment management system is shown, generally designated 10, in one intended environment. As shown, the system 10 includes a general purpose computer 12, such as an IBM-compatible or Apple® brand personal computer having a central processor and memory. A keyboard 13 is electrically connected to the computer 12 for data entry, and display screen 14 is also electrically connected to the computer 12 for presenting a visual display in response to signals from the computer 12.

FIG. 1 also shows that a suitable color printer, preferably a color laser printer 16, is electrically connected to computer 12 for generating hard copy output 18. It will be appreciated by those skilled in the art that computer data entry may be accomplished by data input apparatus other than a keyboard such as voice recognition, scanning, or other data input devices. Likewise, the output media 18 may take various forms other than hard copy computer print-outs, provided such output is capable of being read by the patient.

Software to operate the computer 12 can be stored on a floppy disk 17 which is operably engageable with a floppy disk drive 19 of the computer 12 by means well-known in the art. In accordance with the present invention, the floppy disk 17 is a machine component that includes program code elements which are readable by the computer 12 to render the computer 12 capable of performing method steps for generating a patient medication chart. Alternatively, the program code elements may be stored on other suitable electronic data storage media, including optical disks, hard disk drives, RAM or ROM of the computer 12, and magnetic tape.

Also shown in FIG. 1 is a personalized patient medication chart 20 for managing administration of the patient's medication contained in various medication containers 22. As intended by the present invention, the containers 22 are "original" containers in that they are the actual containers provided to the patient by the pharmacy or other source of medication. The chart 20 can be printed, after undertaking the process below, by the laser printer 16 as hardcopy output 18. Alternatively, the chart 20 can be stored and visualized on electronic media, and/or printed by a printer other than the laser printer 16.

As shown, the personalized medication chart 20 preferably includes a substrate 21 and graphic medication symbols 24 for each patient medication superimposed, as by printing, on the substrate 21. Preferably, the symbols 24 on the chart 20 are colorized, and each symbol 24, as shown, is characterized by a unique combination of alpha-numeric symbol (e.g., a letter), color, and graphic pattern. As intended by the present invention, the symbols 24 on the chart 20 correspond in color, letter, and pattern on a one-to-one basis to graphic medication symbols 25 placed on each container 22.

Figure 2:
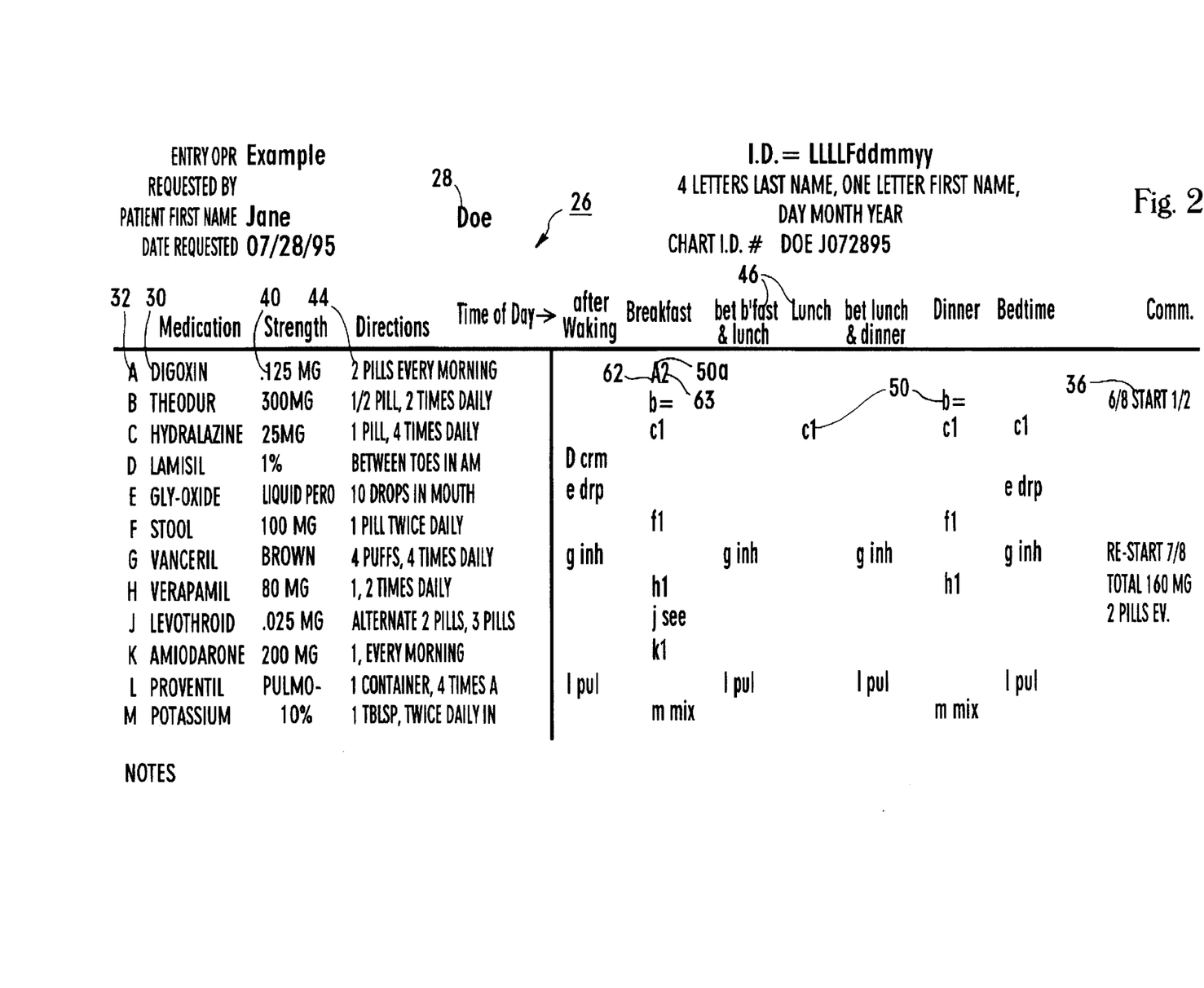
FIG. 2 is a representation of an example of a patient medication data spreadsheet in accordance with the present invention.

Referring now to FIG. 2, there is shown an illustrative example of a set of patient data, generally designated 26, which is entered into system 10 in accordance with the present invention. The patient data 26 is entered by a user into the computer 12 using, e.g., the keyboard 13, and represents the medication treatment regimen for that patient. In the presently preferred embodiment, the patient data 26 is entered into a data base software program which can be stored on the floppy diskette 17 and which accordingly is accessible by the computer 12. In one preferred embodiment, the data 26 is entered using the File-Maker® Pro data base software manufactured by Claris Corporation.

Using information provided by, e.g., a caregiver of the patient, patient data 26 is entered and stored to create a spreadsheet format with row and column identifiers as described herein. As shown in FIG. 2, the patient data 26 includes the patient's name 28, medication name attributes 30, strength attributes 40, directions attributes 44, and alpha-numeric symbol attributes 50.

As can be appreciated in reference to FIG. 2, the electronically entered and stored medication name attributes 30 identify the name of the particular medication, e.g., DIGOXIN®, to be taken by the patient designated by the name 28. Further, each name attribute 30 can include a respective alpha code or letter designation 32, e.g., "A", which is associated with it. In the preferred embodiment shown, the name attributes 30 with respective code or letter designations 32 are arranged in a column entitled "Medication".

As intended herein, the strength attributes 40 are entered by the user and arranged in a column, designated "Strength" in FIG. 2, to specify the amount or strength of the corresponding medication from the "medication" column to be ingested, applied, or otherwise consumed by the patient. Moreover, the user may enter, in a columnar format labelled "directions" in FIG. 2, direction attributes 44 which indicate the scheduled frequency and unit amount of the medication to be taken.

For example, in the first row of the table shown in FIG. 1, the medication having the name attribute "DIGOXIN" is in tablet form, and the corresponding strength attribute 40 indicates that the strength of the medication is one hundred twenty five thousandths milligrams (0.125 mg). Further, the corresponding direction attributes 44 indicate a scheduled frequency and amount of administration of two (2) tablets each morning.

Still referring to FIG. 2, the patient data 26 includes column headings 46 representing various times of day. As shown in FIG. 2, the symbol attributes 50 are arranged in the rows under the column headings 46 as appropriate for the corresponding medications represented by the medication name attributes 32. In other words, the symbol attributes 50 are entered as appropriate for each name attribute 32 to indicate when the medication should be taken. In the preferred embodiment shown in FIG. 2. the column headings 46 include "after waking", "breakfast", "between breakfast and lunch", "lunch", "between lunch and dinner", "dinner", and "bedtime". It is to be understood, however, that the column headings 46 can be other than those shown, and that the headings 46 indeed are personalized for each patient based upon the directions received from the caregiver.

It may now be appreciated that the symbol attributes 50 are alpha-numeric, and are abbreviated representations of the strength of a particular medication for a particular time of day.

For example, under the headings 46 corresponding to "breakfast", "lunch", and "dinner", a symbol attribute 50a of "a2" consists of an alpha portion 62 "a" and numeric portion 63 "2". As more fully disclosed below, the alpha portion 62 "a" identifies by cross-reference the medication as "DIGOXIN", and the numeric portion 63 "2" of the alpha-numeric symbol attribute 50 indicates that two tablets are to be taken at the specified time. Thus, the alpha-numeric symbol attribute "a2" indicates that two DIGOXIN tablets are to be taken at the times indicated by their entry on the spreadsheet, i.e., with breakfast, lunch, and dinner. If desired, comments 36 may be entered in columnar format to correspond with the name attributes 30 under the "medication" column heading.

It is to be noted that the different alpha-numeric medication symbol attributes 50 may include abbreviated designations such as those shown, e.g., where, "crm" is an abbreviation for "cream", "drp" for "drop"; "inh" for "inhale", "inj" for "injection"; "liq" for liquid; "spn" for "spoonful"; "spr" for "spray"; "liq" for "liquid", and the like. This data 26 is thus entered as a spreadsheet based on the prescribed medication treatment plan for the particular patient.

Figure 3:
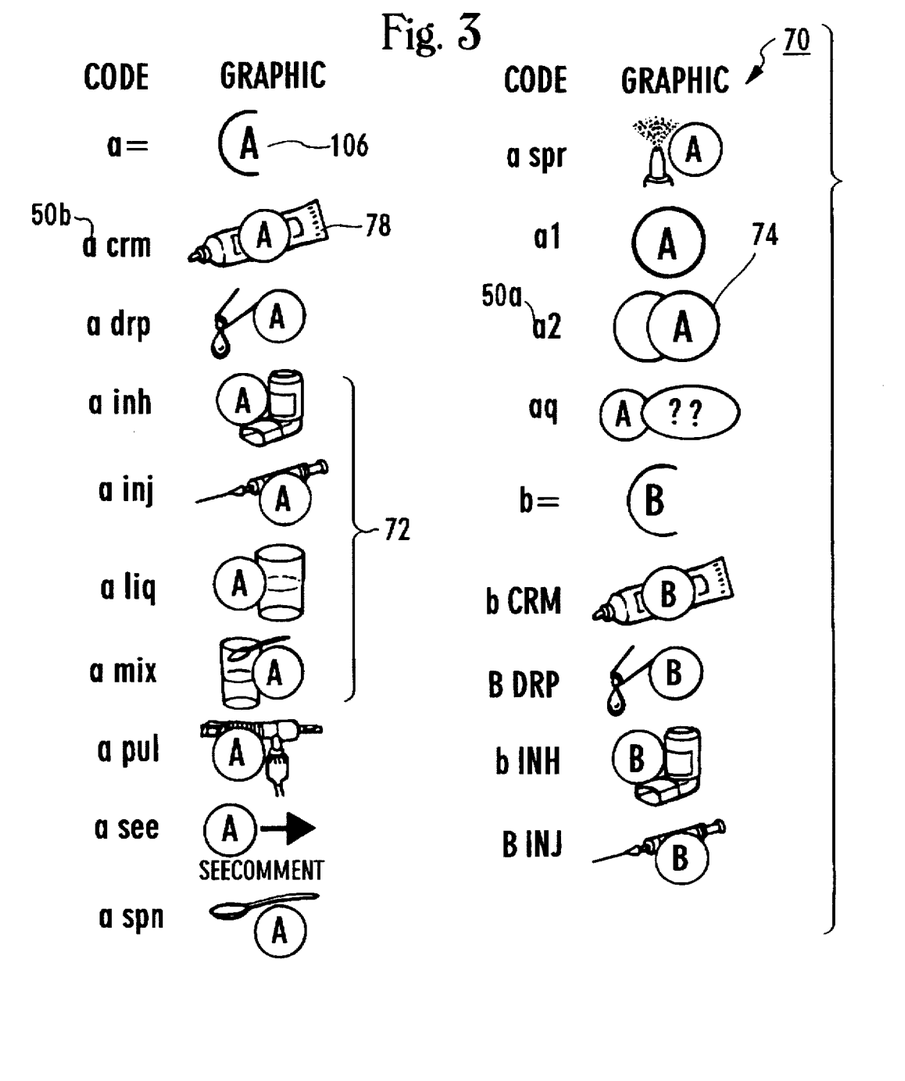
FIG. 3 is a representation of an example of a medication symbol data base for correlating alpha-numeric medication symbol attributes with graphic medication symbols in accordance with the present invention.

Referring now to FIG. 3, there is shown a schematic representation of an electronically stored correlation symbol data table 70 for correlating each alpha-numeric symbol attribute 50 to a respective graphic symbol 72. As shown in FIG. 3. in table 70, the alpha-numeric code 50a "a2" is associated with a corresponding graphic symbol 74 depicting two characters, one of which includes the letter "A" in a circle.

FIG. 3 also shows that other alpha-numeric symbol attributes 50 are associated with respective graphic symbols 74. For example, the symbol attribute 50b of "a crm" indicates medication corresponding to alpha-numeric symbol "a" (i.e., DIGOXIN in the present example) is correlated with graphic symbol 78, which depicts the letter "A" in a circle placed upon an illustration of a tube of medicated cream. It will accordingly be appreciated that the correlation table 70 correlates abbreviated alpha-numeric symbol attributes with graphic symbols.

Figure 4:
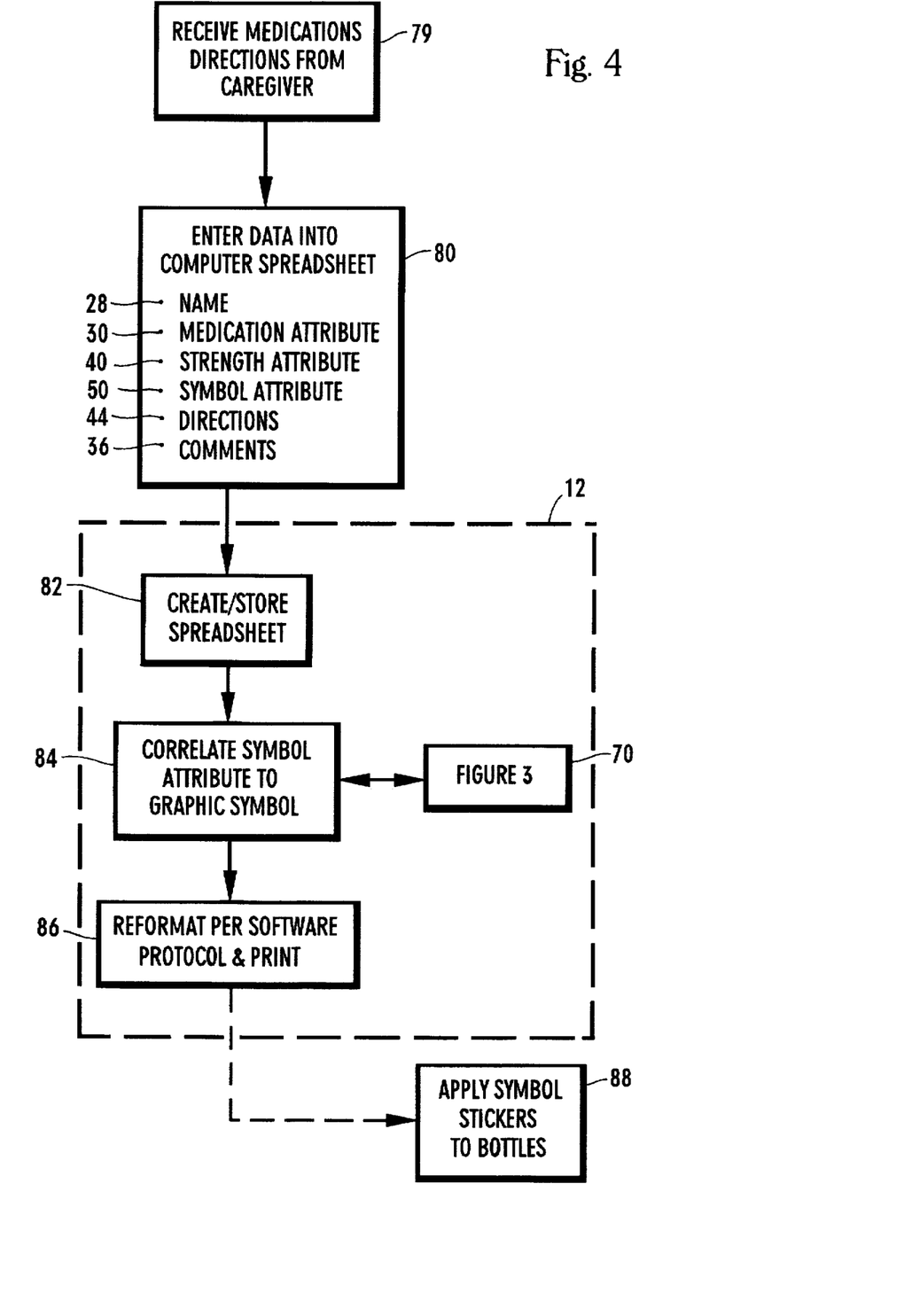
FIG. 4 is a flow chart showing the method of the present invention.
Figure 6:
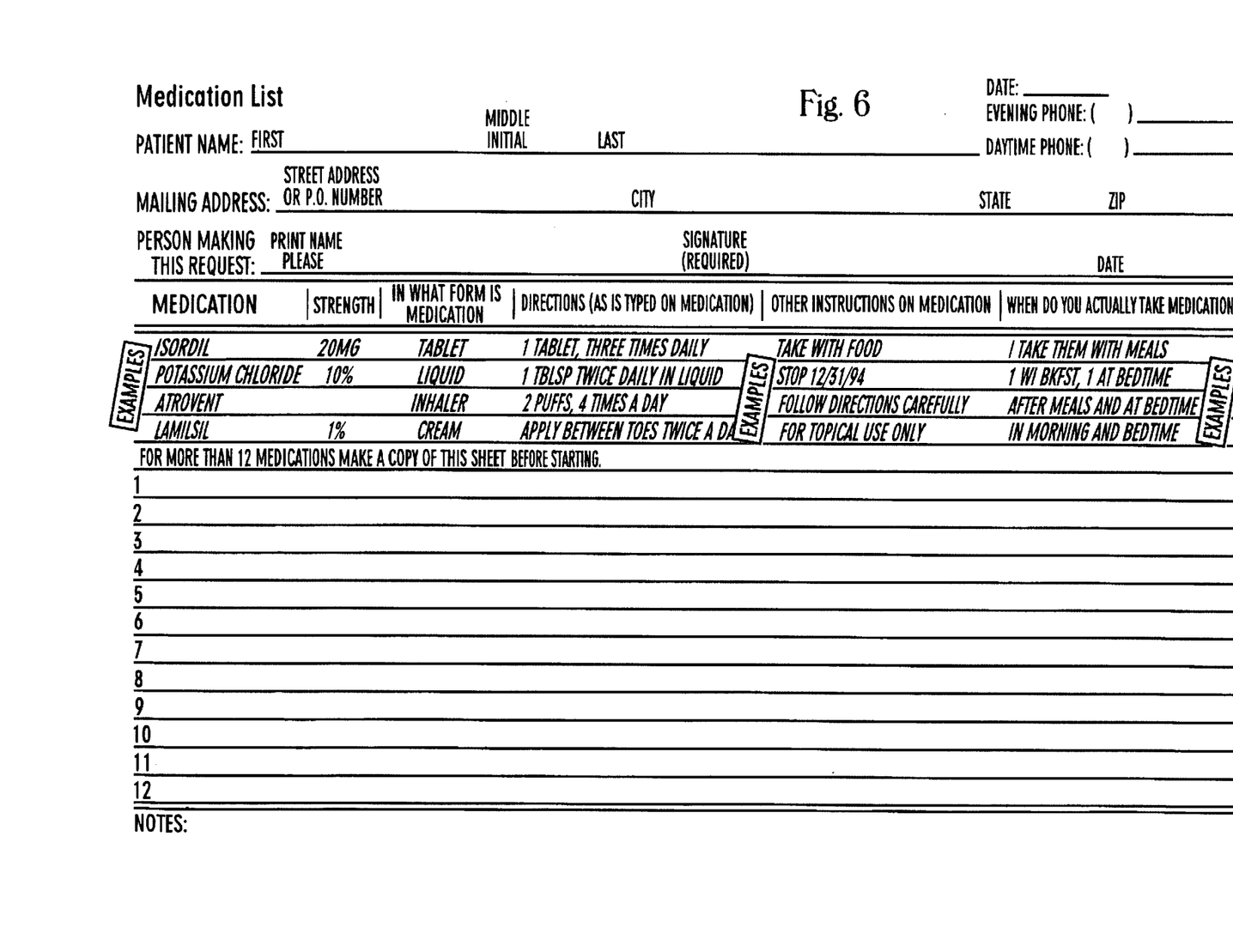
FIG. 6 is an example of a form that can be completed by a caregiver listing treatment directions.

Referring now to FIG. 4, there is shown a schematic diagram of operation of the system and method in accordance with the present invention. Beginning at step 79, medications, strengths, and directions are received from, e.g., a caregiver of the patient. Referring briefly to FIG. 6, a preferred caregiver form is shown which is completed by a caregiver, although it is to be understood that other formats for caregiver directions may be used.

At step 80, the patient data 26 is entered using a data base program into computer 12. As disclosed above, the patient data 26 includes the patient name 28, medication name attributes 30, strength attributes 40, and alpha-numeric symbol attributes 50, as well as any relevant administration comments 36. The administration comments 36 provide a means for indicating unusual directions from the caregiver which otherwise cannot be shown graphically. Further, during the data entry at step 80, the time of day headings 46 are established as required by the caregiver instructions.

Next, at step 82, the entered information 26 is stored by the computer 12 in a spreadsheet format created per the software protocol. The spreadsheet may be viewed on the screen 14 of the computer 12, or printed out, or both.

From step 82, the system 10 proceeds to step 84, wherein the computer 12 accesses the data base 70 to associate the entered alpha-numeric symbol attributes 50 with corresponding graphic symbols 72. At step 86, the data base software program used by the computer 12 causes the computer 12 to generate an electronic and/or hard copy output in the form of the personalized patient medication management chart 20 shown in FIG. 1. It is to be understood that the graphics symbols 72 generated at step 84 establish the symbols 24 that are printed on the patient chart 20 shown in FIG. 1.

Further, the graphics symbols 72 generated at step 84 establish the symbols 25 that are associated with the containers 22 shown in FIG. 1. Accordingly, at step 88, the symbols 25 shown in FIG. 1 are printed as self-adhesive labels and then adhesively applied to the appropriate containers 22.

Figure 5A:
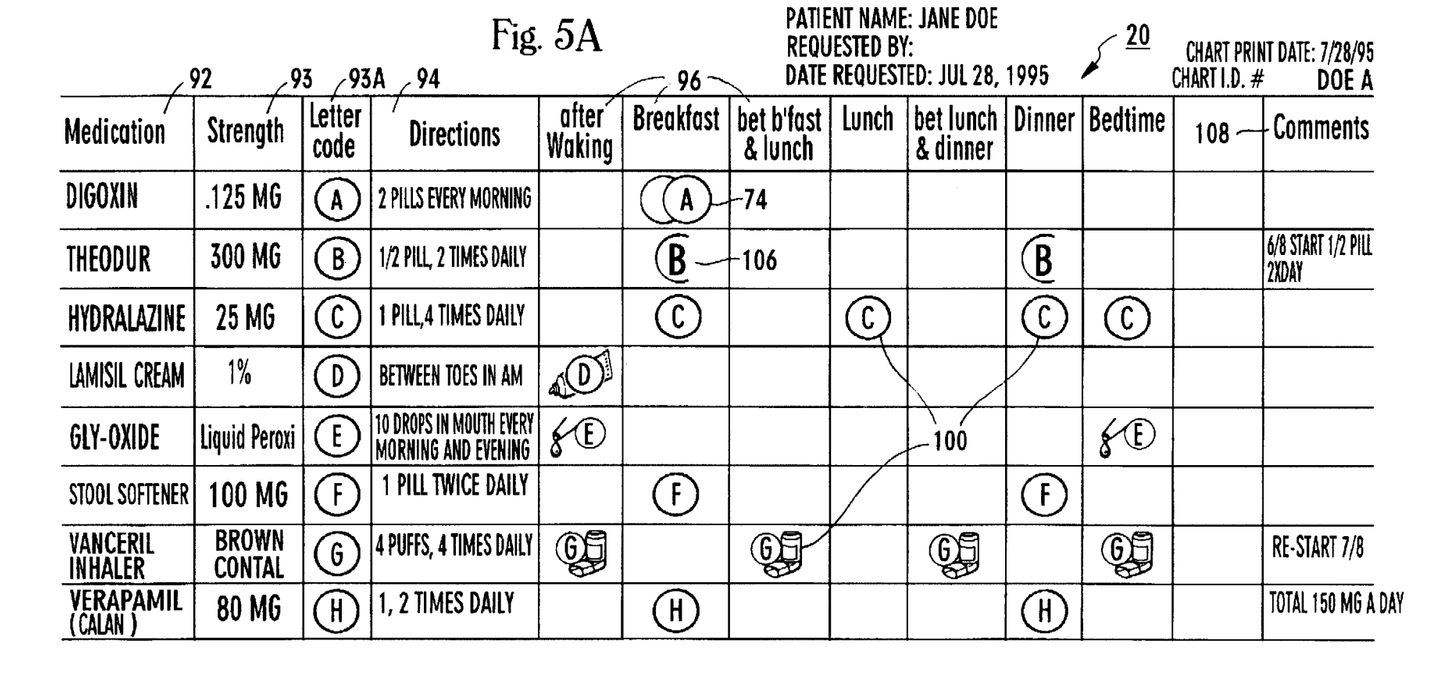
FIG. 5 is a representation of an example of a personalized patient medication administration management chart in accordance with the present invention.
Figure 5B:
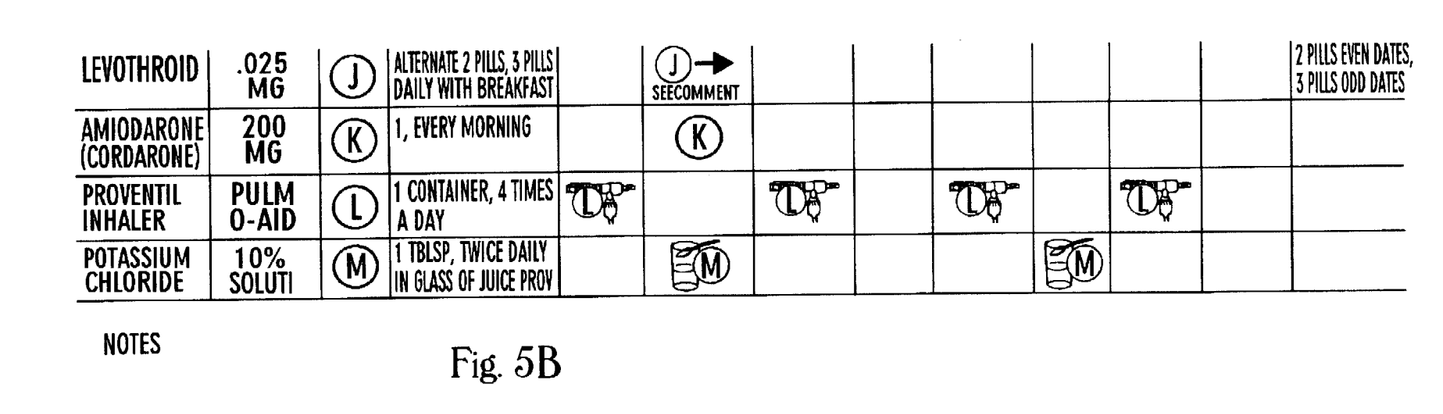

Referring now to FIG. 5, the details of the personalized patient medication management chart 20 can be seen. As can be appreciated in reference to FIG. 5, the chart 20 includes an easy-to-read tabular visual display of necessary patient information. As shown, the chart 20 includes the name of the patient and any associated patient identification as input at step 80 in FIG. 4.

Additionally, the chart 20 includes a medication column 92, entitled "Medication" in FIG. 5. It is to be understood that the entries in the medication column 92 are established by the medication attributes 30 input at block 80 of FIG. 4. Further, the chart 20 includes a strength column 93, under the heading of which are listed strengths that correspond to the medications set forth in the medication column 92. Thus, each of the entries in the strength column 93 is visually associated as shown with a respective entry in the medication column 92. It is to be understood that the entries in the strength column 93 are established by the strength attributes 40 input at block 80 of FIG. 4.

Moreover, the chart 20 includes a graphic code column 93A, which sets forth graphic symbols as shown. Each of the entries in the graphic code column 93A is visually associated as shown with a respective entry in the medication column 92.

FIG. 5 shows that the chart 20 also includes a directions column 94, indicating directions for consuming respective medications in the medications column 92. It is to be understood that the entries in the directions column 94 are established by the directions attributes 44 input at block 80 of FIG. 4.

Also, the chart 20 includes at least one time of day column 96, as established at step 80 in FIG. 4. As shown, graphic symbols, generally indicated as 100, are displayed in the appropriate time of day columns 96. Graphic symbols 100 also convey additional information. For example, when two pills of a particular medication are required to be administered each time, the graphic symbol 74, representing two pills, can be displayed. Or, if half of a pill is indicated, a graphic symbol 106 representing one-half of a pill is visually displayed in chart 20. In any case, it is to be understood that the graphics symbols 100 displayed on the chart 20 are established by the graphics symbols shown in FIG. 3 and, hence, by the symbol attributes 50 entered at block 80 in FIG. 4.

FIG. 5 also shows that the chart 20 includes a comments column 108. Each of the entries in the comments column 108 is visually associated as shown with a respective entry in the medication column 92. It is to be understood that the entries in the comments column 108 are established by the comments 36 input at block 80 of FIG. 4.

As disclosed above, the system 10 includes adhesive graphic symbol labels 25 which correspond to the symbol entries in the symbol column 93A. The labels 25 are applied to the corresponding "original" medication container 22. This is illustrated in FIG. 1, in which the various containers, e.g., bottles, tubes, etc. of medication 22 display the appropriate symbol 25 corresponding to the symbol 24 on the chart 20. Consequently, the present invention advantageously permits use of original medication containers in conjunction with the chart 20. In the case of changes to a patient's regimen, the patient data 26 can be revised as needed on computer 12, and a new chart 20 can then quickly and efficiently be electronically generated.

While the particular SYSTEM AND METHOD FOR PERSONALIZED MEDICATION TREATMENT MANAGEMENT as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly limited by nothing other than the appended claims.

What is claimed is:

1. A method for generating a medication management display, comprising the steps of:
    (a) entering a plurality of medication name attributes into an electronic data base, each name attribute representing a respective medication;
    (b) for each name attribute, entering a corresponding strength attribute into the database;
    (c) for each name attribute, entering a corresponding alpha-numeric symbol attribute into the database;
    (d) accessing an electronically stored correlation list to associate the alpha-numeric symbol attribute to a graphic symbol; and
    (e) generating a visual display including one or more of the name attributes, wherein each displayed name attribute is visually associated with its corresponding strength attributes and graphic symbol.

2. The method of claim 1, further comprising the step of entering each symbol attribute in one or more columns having corresponding displayed time columns, wherein the symbol is visually displayed in one or more displayed time columns.

3. The method of claim 1, further comprising the step of associating administration comments with at least one medication and visually displaying the comments.

4. The method of claim 2, wherein each medication is held in an associated container, and the method further comprises the step of visually associating one of the graphic symbols on a respective container.

5. A system for generating a medication management display, comprising:
    (a) medication name means for entering a plurality of name attributes into an electronic data base, each name attribute representing a respective medication;
    (b) strength attribute means for entering into the database a strength attribute corresponding to each name attribute;
    (c) alpha-numeric symbol attribute means for entering into the database an alpha-numeric symbol attribute corresponding to each name attribute;
    (d) correlation means for accessing an electronically stored correlation list to associate the alpha-numeric symbol attribute to a graphic symbol; and
    (e) display means for generating a visual display including one or more of the name attributes, wherein each displayed name attribute is visually associated with its corresponding strength attributes and graphic symbol.

6. The system of claim 5, further comprising means for entering each alpha-numeric symbol attribute in one or more columns having corresponding displayed time columns, wherein the symbol is visually displayed in one or more displayed time columns.

7. The system of claim 5, further comprising means for associating administration comments with at least one medication and visually displaying the comments.

8. The system of claim 5, wherein each medication is held in an associated container, and the system further comprises means for visually associating one of the graphic symbols on a respective container.

* * * * *